US008465467B2

(12) United States Patent
Gao

(10) Patent No.: US 8,465,467 B2
(45) Date of Patent: Jun. 18, 2013

(54) METHOD OF CONTROLLING AN IRRIGATION/ASPIRATION SYSTEM

(75) Inventor: Shawn X. Gao, Irvine, CA (US)

(73) Assignee: Novartis AG, Basel (CH)

( * ) Notice: Subject to any disclaimer, the term of this patent is extended or adjusted under 35 U.S.C. 154(b) by 1447 days.

(21) Appl. No.: 11/521,583

(22) Filed: Sep. 14, 2006

(65) Prior Publication Data

US 2008/0125697 A1    May 29, 2008

(51) Int. Cl.
*A61M 31/00* (2006.01)
*A61M 1/00* (2006.01)

(52) U.S. Cl.
USPC .......................................... 604/503; 604/118

(58) Field of Classification Search
USPC .............. 604/65–67, 118–121, 503
See application file for complete search history.

(56) References Cited

U.S. PATENT DOCUMENTS

| | | | |
|---|---|---|---|
| 3,288,385 A | 11/1966 | Markakis et al. |
| 3,589,363 A | 6/1971 | Banko et al. |
| 3,615,155 A | 10/1971 | Gelbman |
| 3,674,942 A | 7/1972 | Sugaya et al. |
| 3,812,855 A * | 5/1974 | Banko | 604/31 |
| 3,861,619 A | 1/1975 | Wolff |
| 3,881,483 A | 5/1975 | Sausse |
| 3,982,540 A | 9/1976 | Ross |
| 4,029,094 A | 6/1977 | Winicki |
| 4,041,947 A | 8/1977 | Weiss et al. |
| 4,052,987 A | 10/1977 | Wuchinich et al. |
| 4,058,123 A | 11/1977 | May |
| 4,140,118 A | 2/1979 | Jassawalla |
| 4,180,074 A * | 12/1979 | Murry et al. | 604/31 |
| 4,184,510 A | 1/1980 | Murry et al. |
| 4,187,057 A | 2/1980 | Xanthopoulous |
| 4,210,029 A | 7/1980 | Porter |
| 4,223,676 A | 9/1980 | Wuchinich et al. |
| 4,223,813 A | 9/1980 | Garrett et al. |
| 4,246,902 A | 1/1981 | Martinez |
| 4,395,258 A | 7/1983 | Wang et al. |
| 4,398,542 A | 8/1983 | Cunningham et al. |
| 4,399,332 A | 8/1983 | Furlan et al. |
| 4,444,548 A | 4/1984 | Andersen et al. |
| 4,475,904 A | 10/1984 | Wang |
| 4,479,761 A | 10/1984 | Bilstad et al. |
| 4,493,694 A | 1/1985 | Wuchinich |
| 4,493,695 A | 1/1985 | Cook |
| 4,493,706 A | 1/1985 | Borsanyi et al. |
| 4,515,583 A | 5/1985 | Sorich |
| 4,526,515 A | 7/1985 | DeVries |

(Continued)

FOREIGN PATENT DOCUMENTS

EP    0 319 273 A1    6/1989
EP    0 319 273 B1    9/1991

(Continued)

OTHER PUBLICATIONS

Mark A. Hopkins, et al., Aspiration Control Via Flow or Impedence, U.S. Appl. No. 12/545,392, filed Aug. 21, 2009 (13 pages).

*Primary Examiner* — Kevin C Sirmons
*Assistant Examiner* — Andrew Gilbert

(57) ABSTRACT

A dual pump aspiration system having both a vacuum level control loop and a flow rate control loop. The system can be operated either as a vacuum priority system or a flow rate priority system.

19 Claims, 1 Drawing Sheet

U.S. PATENT DOCUMENTS

| | | |
|---|---|---|
| 4,530,647 A | 7/1985 | Uno |
| 4,537,561 A | 8/1985 | Xanthoupoulos |
| 4,548,205 A | 10/1985 | Armeniades et al. |
| 4,550,247 A | 10/1985 | Winter et al. |
| 4,589,415 A | 5/1986 | Haaga |
| 4,609,368 A | 9/1986 | Dotson, Jr. |
| 4,626,248 A | 12/1986 | Scheller |
| 4,627,833 A | 12/1986 | Cook |
| 4,650,462 A * | 3/1987 | DeSatnick et al. ............... 604/30 |
| 4,670,006 A | 6/1987 | Sinnett et al. |
| 4,712,907 A | 12/1987 | Weinberger et al. |
| 4,713,051 A | 12/1987 | Steppe et al. |
| 4,722,350 A | 2/1988 | Armeniades et al. |
| 4,735,610 A | 4/1988 | Akkas et al. |
| 4,758,220 A | 7/1988 | Sundblom et al. |
| 4,758,238 A | 7/1988 | Sundblom et al. |
| 4,768,547 A | 9/1988 | Danby et al. |
| 4,770,187 A | 9/1988 | Lash et al. |
| 4,773,897 A | 9/1988 | Scheller et al. |
| 4,790,816 A | 12/1988 | Sundblom et al. |
| 4,798,580 A | 1/1989 | DeMeo et al. |
| 4,810,242 A | 3/1989 | Sundblom et al. |
| 4,813,927 A | 3/1989 | Morris et al. |
| 4,823,552 A | 4/1989 | Ezell et al. |
| 4,832,685 A | 5/1989 | Haines |
| 4,838,865 A | 6/1989 | Flank et al. |
| 4,841,984 A | 6/1989 | Armeniades et al. |
| 4,861,242 A | 8/1989 | Finsterwald |
| 4,869,715 A | 9/1989 | Sherburne |
| 4,878,896 A | 11/1989 | Garrison et al. |
| 4,900,301 A | 2/1990 | Morris et al. |
| 4,902,277 A * | 2/1990 | Mathies et al. ................ 604/67 |
| 4,909,786 A | 3/1990 | Gijselhart et al. |
| 4,921,477 A | 5/1990 | Davis |
| 4,922,902 A | 5/1990 | Wuchinich et al. |
| 4,923,375 A | 5/1990 | Ejlerson et al. |
| 4,935,005 A | 6/1990 | Haines |
| 4,950,016 A | 8/1990 | Kumar |
| 4,963,131 A | 10/1990 | Wortrich |
| 4,989,583 A | 2/1991 | Hood |
| 5,020,535 A | 6/1991 | Parker et al. |
| 5,032,111 A | 7/1991 | Morris et al. |
| 5,041,096 A | 8/1991 | Beuchat et al. |
| 5,047,009 A | 9/1991 | Morris et al. |
| 5,098,387 A | 3/1992 | Weiss et al. |
| 5,106,366 A | 4/1992 | Steppe |
| 5,125,891 A | 6/1992 | Hossain et al. |
| 5,141,493 A | 8/1992 | Jacobsen et al. |
| 5,154,694 A | 10/1992 | Kelman |
| 5,160,317 A | 11/1992 | Costin |
| 5,163,900 A | 11/1992 | Wortrich |
| 5,179,606 A | 1/1993 | Kaihara et al. |
| 5,195,960 A | 3/1993 | Hossain et al. |
| 5,207,647 A | 5/1993 | Phelps |
| 5,242,404 A | 9/1993 | Conley et al. |
| 5,246,422 A | 9/1993 | Favre |
| 5,267,956 A | 12/1993 | Beuchat |
| 5,279,547 A | 1/1994 | Costin |
| 5,322,504 A | 6/1994 | Doherty et al. |
| 5,330,431 A | 7/1994 | Herskowitz |
| 5,342,293 A | 8/1994 | Zanger |
| 5,342,313 A | 8/1994 | Campbell et al. |
| 5,364,342 A | 11/1994 | Beuchat et al. |
| 5,380,280 A | 1/1995 | Peterson |
| 5,399,166 A | 3/1995 | Laing |
| 5,403,276 A * | 4/1995 | Schechter et al. ............... 604/22 |
| 5,403,277 A | 4/1995 | Dodge et al. |
| 5,424,040 A | 6/1995 | Bjornsson |
| 5,429,601 A * | 7/1995 | Conley et al. ................... 604/65 |
| 5,429,602 A | 7/1995 | Hauser |
| 5,436,418 A | 7/1995 | Tamehira |
| 5,460,490 A | 10/1995 | Carr et al. |
| 5,470,312 A | 11/1995 | Zanger et al. |
| 5,499,969 A | 3/1996 | Beuchat et al. |
| 5,518,378 A | 5/1996 | Neftel et al. |
| 5,520,633 A | 5/1996 | Costin |
| 5,549,139 A | 8/1996 | Perkins et al. |
| 5,554,112 A | 9/1996 | Walbrink et al. |
| 5,556,378 A * | 9/1996 | Storz et al. ...................... 604/31 |
| 5,586,973 A * | 12/1996 | Lemaire et al. ................ 604/31 |
| 5,588,815 A | 12/1996 | Zaleski, II |
| 5,591,127 A | 1/1997 | Barwick, Jr. et al. |
| 5,616,121 A * | 4/1997 | McKay .......................... 604/35 |
| 5,656,027 A * | 8/1997 | Ellingboe ..................... 604/541 |
| 5,668,611 A | 9/1997 | Ernstoff et al. |
| 5,674,194 A | 10/1997 | Jung et al. |
| 5,676,530 A | 10/1997 | Nazarifar |
| 5,676,650 A | 10/1997 | Grieshaber et al. |
| 5,685,840 A | 11/1997 | Schechter et al. |
| 5,697,898 A | 12/1997 | Devine |
| 5,700,240 A | 12/1997 | Barwick, Jr. et al. |
| 5,704,927 A | 1/1998 | Gillette et al. |
| 5,709,539 A | 1/1998 | Hammer et al. |
| 5,733,256 A | 3/1998 | Costin |
| 5,746,708 A | 5/1998 | Giesler et al. |
| 5,747,824 A * | 5/1998 | Jung et al. .................... 250/577 |
| 5,759,017 A | 6/1998 | Patton et al. |
| 5,766,146 A | 6/1998 | Barwick, Jr. |
| 5,836,909 A * | 11/1998 | Cosmescu ....................... 604/35 |
| 5,865,764 A | 2/1999 | Moorhead |
| 5,897,524 A | 4/1999 | Wortrich et al. |
| 5,899,674 A | 5/1999 | Jung et al. |
| 5,906,598 A | 5/1999 | Giesler et al. |
| 5,910,110 A | 6/1999 | Bastable |
| 5,927,956 A | 7/1999 | Lim et al. |
| 5,996,634 A | 12/1999 | Dennehey et al. |
| 6,012,999 A | 1/2000 | Patterson |
| 6,059,544 A | 5/2000 | Jung et al. |
| 6,083,193 A | 7/2000 | Kadziauskas et al. |
| 6,129,699 A | 10/2000 | Haight et al. |
| 6,179,808 B1 | 1/2001 | Boukhny et al. |
| 6,186,975 B1 | 2/2001 | Sakai |
| 6,224,345 B1 | 5/2001 | Dussault |
| 6,251,113 B1 | 6/2001 | Appelbaum et al. |
| 6,261,283 B1 | 7/2001 | Morgan et al. |
| 6,283,937 B1 * | 9/2001 | Takamatsu et al. ............. 604/31 |
| 6,293,926 B1 | 9/2001 | Sorenson et al. |
| 6,413,022 B1 | 7/2002 | Sarh |
| 6,635,028 B1 | 10/2003 | Ielpo et al. |
| 6,719,717 B1 | 4/2004 | Johnson et al. |
| 6,743,636 B2 | 6/2004 | Chung et al. |
| 6,955,526 B2 | 10/2005 | Yamazaki et al. |
| 6,997,896 B2 * | 2/2006 | Novak ............................ 604/67 |
| 7,524,299 B2 * | 4/2009 | Hopkins et al. ................. 604/30 |
| 8,246,580 B2 * | 8/2012 | Hopkins et al. ............... 604/118 |
| 2002/0019607 A1 * | 2/2002 | Bui ................................. 604/67 |
| 2002/0055725 A1 | 5/2002 | Verkaart et al. |
| 2002/0151836 A1 | 10/2002 | Burden |
| 2003/0204172 A1 | 10/2003 | Steppe |
| 2006/0224143 A1 | 10/2006 | Claus et al. |
| 2007/0005029 A1 * | 1/2007 | Hopkins et al. ............... 604/317 |
| 2007/0005030 A1 * | 1/2007 | Hopkins et al. ............... 604/317 |
| 2007/0021713 A1 * | 1/2007 | Kumar et al. ................... 604/27 |

FOREIGN PATENT DOCUMENTS

| | | |
|---|---|---|
| EP | 0 320 168 B1 | 7/1993 |
| EP | 1310267 A2 | 5/2003 |
| EP | 1900347 A1 | 3/2008 |
| EP | 1900347 B1 | 4/2009 |
| EP | 2065020 A1 | 6/2009 |
| FR | 2 466 641 A1 | 4/1981 |
| FR | 2 727 847 A1 | 6/1996 |
| GB | 2 176 717 A | 1/1987 |
| JP | 64-085647 | 3/1989 |
| JP | 06-335523 | 12/1994 |
| WO | WO 90/08562 A1 | 8/1990 |
| WO | WO 9218049 A1 | 10/1992 |
| WO | WO 9317729 A1 | 9/1993 |
| WO | WO 9318802 A1 | 9/1993 |
| WO | WO 95/28190 A1 | 10/1995 |
| WO | WO 99/45868 A1 | 9/1999 |
| WO | WO 00/27275 A1 | 5/2000 |
| WO | WO 2007/001503 A2 | 1/2007 |
| WO | WO 2007/001503 A3 | 1/2007 |

* cited by examiner

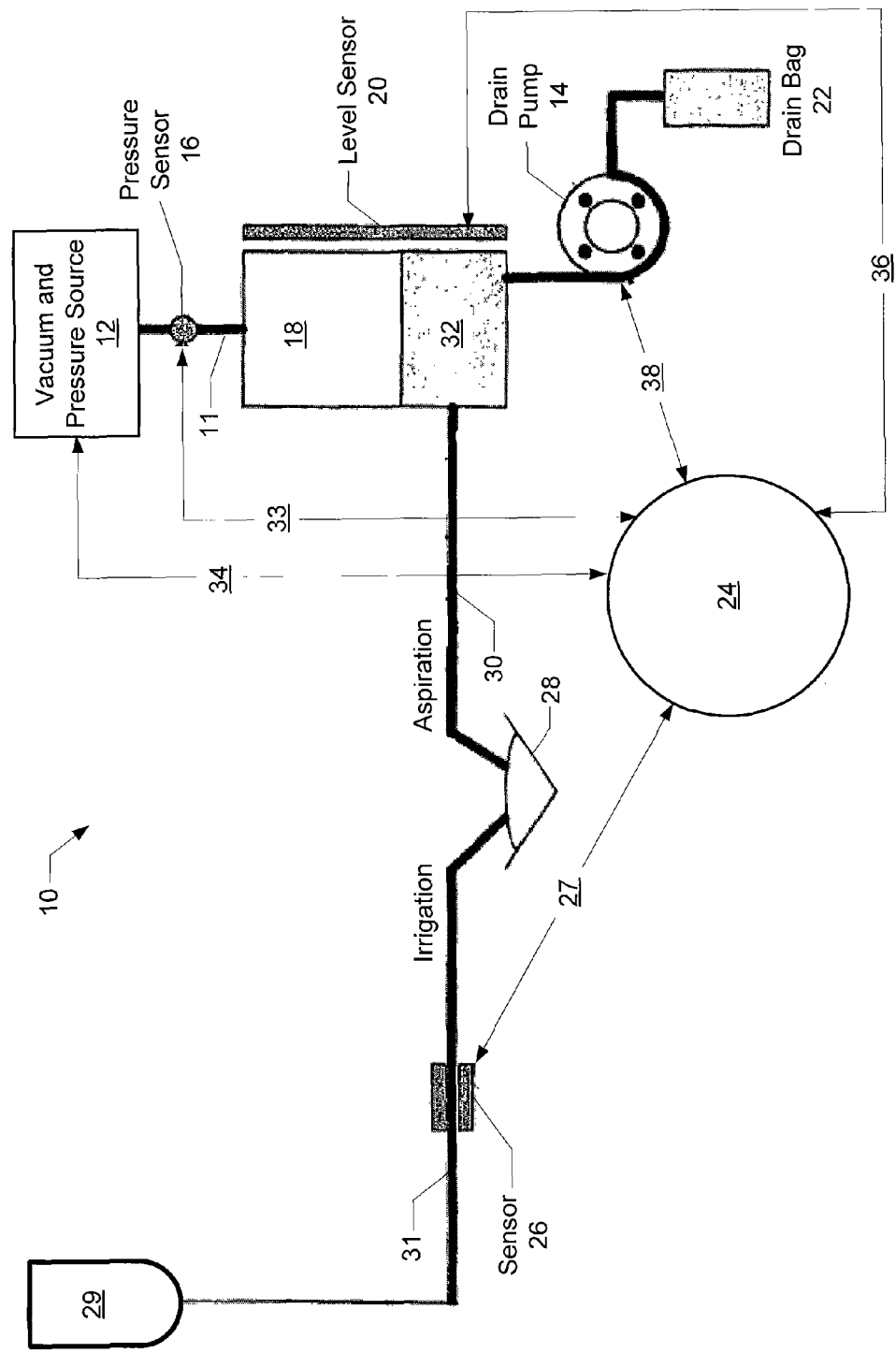

METHOD OF CONTROLLING AN IRRIGATION/ASPIRATION SYSTEM

This invention relates to surgical control consoles and more particularly to irrigation/aspiration systems used in surgical control consoles.

BACKGROUND OF THE INVENTION

During small incision surgery, and particularly during ophthalmic surgery, small probes are inserted into the operative site to cut, remove or otherwise manipulate tissue. During these surgical procedures, the surgical site typically is flushed with an irrigating solution and the irrigating solution and tissue is aspirated from the surgical site. The types of aspiration system used, prior to the present invention, where generally characterized as either flow controlled or vacuum controlled, depending upon the type of pump used in the system, and each type of system has certain advantages.

Vacuum controlled aspiration systems are operated by setting a desired vacuum level, which the system seeks to maintain. Flow rate information is not available directly. Vacuum controlled aspiration systems typically use a venturi or diaphragm pump. Vacuum controlled aspiration systems offer the advantages of quick response times, control of decreasing vacuum levels and good fluidic performance while aspirating air, such as during an air/fluid exchange procedure.

Disadvantages of such systems are the lack of flow information resulting in high flows during phacoemulsification/ fragmentation coupled with a lack of occlusion detection. Vacuum controlled systems are difficult to operate in a flow controlled mode because of the problem of non-invasively measuring flow in real time.

Flow controlled aspiration systems are operated by setting a desired aspiration flow rate for the system to maintain. Flow controlled aspiration systems typically use a peristaltic, scroll or vane pump. Flow controlled aspiration systems offer the advantages of stable flow rates and automatically increasing vacuum levels under occlusion. Disadvantages of such systems are relatively slow response times, undesired occlusion break responses when large compliance components are used and vacuum can not be linearly decreased during tip occlusion. In addition, peristaltic pumps produce pulsations in the aspiration fluid flow. When such pumps are in fluid communication with a surgical site, these pump pulsations can be manifested at the surgical site. Flow controlled systems are difficult to operate in a vacuum controlled mode because time delays in measuring vacuum can cause instability in the control loop, reducing dynamic performance.

One surgical system currently commercially available, the Millennium from Storz Instrument Company, contains both a vacuum controlled aspiration system (using a venturi pump) and a flow controlled aspiration system (using a scroll pump). The two pumps can not be used simultaneously, and each pump requires separate aspiration tubing and cassette.

Another currently available system, the ACCURUS® system from Alcon Laboratories, Inc., contains both a venturi pump and a peristaltic pump that operate in series. The venturi pump aspirates material from the surgical site to a small collection chamber. The peristaltic pump pumps the aspirate from the small collection chamber to a larger collection bag. The peristaltic pump does not provide aspiration vacuum to the surgical site. Thus, the system operates as a vacuum controlled system.

Accordingly, a need continues to exist for a surgical system that operates in both vacuum controlled and flow controlled modes.

BRIEF SUMMARY OF THE INVENTION

The present invention improves upon prior art by providing a dual pump aspiration system having both a vacuum level control loop and a flow rate control loop. The system can be operated either as a vacuum priority system or a flow rate priority system.

Accordingly, an objective of the present invention to provide a dual pump aspiration system.

Another objective of the present invention to provide an aspiration system having both a vacuum level control loop and a flow rate control loop.

A further objective of the present invention to provide an aspiration control system and method that can be operated either as a vacuum priority system or a flow rate priority system.

Other objectives, features and advantages of the present invention will become apparent with reference to the drawings, and the following description of the drawings and claims.

BRIEF DESCRIPTION OF THE DRAWINGS

The FIGURE is a schematic diagram of the dual mode system of the present invention.

DETAILED DESCRIPTION OF THE INVENTION

As best seen in the FIGURE, system 10 of the present invention generally contains vacuum pump 12, flow pump 14, pressure transducer 16, small collection chamber 18, fluid level sensor 20, drain bag 22, control circuitry 24 and sensor 26, such as a flow or pressure sensors. Vacuum pump 12 may be any suitable pump, such as a diaphragm pump, a vane pump, a scroll pump or a peristaltic pump, but a venturi pump is preferred. Pressure transducer 16 may be any suitable device for directly or indirectly measuring pressure or vacuum, such as a vacuum transducer or an absolute pressure transducer. One suitable system for controlling vacuum pump 12 is disclosed in U.S. Pat. No. 5,674,194, the entire contents of which being incorporated herein by reference. Flow pump 14 may be any suitable pump, such as a venturi pump, a diaphragm pump, a vane pump or a scroll pump, but a peristaltic pump is preferred. Fluid level sensor 20 may be any suitable device for measuring the fluid level in small collection chamber 18, but an optical fluid or acoustic level sensor, such as the one described in U.S. Pat. No. 5,747,824, the entire contents of which being incorporated herein by reference, is preferred. Control circuitry 24 contains all of the necessary hardware and software to control system 10, such hardware and software being well within the ordinary skill of those in the art.

In vacuum controlled, system 10 operates by vacuum pump 12 drawing a preselected vacuum in small chamber 18 through aspiration line 11. This vacuum is transmitted to surgical site 28 through aspiration line 30. As small chamber 18 begins to fill with fluid 32, changes in the vacuum level are sensed by pressure transducer 16, which sends a signal to control circuitry 24 through interface 33. Control circuitry 24 communicates a control signal to vacuum pump 12 through interface 34 to adjust the vacuum supplied by vacuum pump 12 as required. When the level of fluid 32 in small chamber 18 reaches a preselected level, fluid level sensor 20 sends a signal to control circuitry 24 through interface 36. Control circuitry 24 generates a flow pump control signal and communicates the signal to flow pump 14 through interface 38, directing flow pump 14 to begin evacuating fluid 32 from small chamber 18 through line 40 and into drain bag 22. The operation of system 10, under the direction of control circuitry 24, maintains a steady pressure level in aspiration line 30.

In flow controlled mode, system 10 operates by vacuum pump 12 drawing a vacuum in small chamber 18 through aspiration line 11. This vacuum is transmitted to surgical site 28 through aspiration line 30. The vacuum at surgical site 28, along with the pressurization of the infusion fluid cause by elevating or pressurizing irrigation fluid source 29 causes irrigation fluid 32 to flow to surgical site 28 through irrigation line 31. The flow rate or pressure within irrigation line 31 can be measured by sensor 26, and communicated to control circuitry 24 through interface 27. Irrigation fluid 32 continues to flow to surgical site 28 and out of surgical site 28 to small chamber 18 through aspiration line 30. As small chamber 18 begins to fill with fluid 32, changes in the vacuum level are sensed by pressure transducer 16, which sends a signal to control circuitry 24 through interface 33 and changes in the fluid level are detected by fluid level sensor 20, which sends a signal to control circuitry 24 through interface 36. With the information from fluid level sensor 20, flow pump 14 and sensor 26, control circuitry 24 can estimate aspiration fluid flow in aspiration line 30. Control circuitry 24, therefore, can control system 10 based on the calculated aspiration flow rather than aspiration pressure. One skilled in the art will understand that by varying the vacuum in collection chamber 18, the flow through aspiration line 30 can be controlled. In addition, by comparing calculated aspiration fluid flow and measured irrigation fluid flow, control circuitry can detect a number of events, such as amount of wound leakage at surgical site 28, obstructions in irrigation line 31 and obstructions or occlusions in aspiration line 30.

One skilled in the art will recognize that hybrid control modes may also be used, wherein system 10 operates in flow control mode unless certain conditions are present in which case system 10 begins operating in vacuum control mode or visa versa.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. A method of controlling an irrigation/aspiration system, the system having an irrigation line, an irrigation flow sensor and a vacuum pump, the vacuum pump communicating with a surgical site through a collection chamber and an aspiration line, the method comprising:
   a) connecting the irrigation line to a source of irrigation fluid;
   b) operating the vacuum pump so as to introduce a vacuum into the collection chamber so as to draw an irrigation fluid from the source of irrigation fluid through the irrigation line, the surgical site and the aspiration line and into the collection chamber;
   c) adjusting a level of fluid in the collection chamber by using a flow pump and/or the vacuum pump;
   d) monitoring a flow of the irrigation fluid in the irrigation line with the flow sensor;
   e) monitoring the fluid level in the collection chamber using a fluid level sensor;
   f) monitoring the vacuum in the collection chamber from the vacuum pump; and
   g) varying the vacuum introduced into the chamber based on the monitored irrigation fluid flow and the monitored fluid level in the collection chamber so as to maintain fluid flow into the chamber through the aspiration line at a selected flow rate.

2. The method of claim 1, wherein maintaining the fluid flow at the selected flow rate is implemented for the system in a flow rate control mode and wherein the method further comprises implementing a vacuum control mode.

3. The method of claim 2, wherein implementing the vacuum control mode comprises varying the vacuum introduced into the collection chamber based on the monitored vacuum pressure and the monitored fluid level in the collection chamber so as to maintain a steady pressure level in the aspiration line.

4. The method of claim 1, further comprising calculating an aspiration fluid flow in the aspiration line.

5. The method of claim 4, wherein calculating the aspiration fluid flow comprises using the monitored irrigation fluid flow or pressure, the monitored vacuum pressure, and/or the monitored fluid level in the collection chamber.

6. The method of claim 4, further comprising comparing the calculated aspiration fluid flow and the monitored irrigation fluid flow to determine an amount of leakage of the irrigation fluid at the surgical site.

7. The method of claim 4, further comprising comparing the calculated aspiration fluid flow and the monitored irrigation fluid flow to determine when an obstruction has occurred in the irrigation line or the aspiration line.

8. The method of claim 4, further comprising controlling the flow of irrigation fluid at the surgical site without introducing pulsations to the surgical site through the aspiration line at least in part by comparing the calculated aspiration fluid flow and the monitored irrigation fluid flow.

9. The method of claim 2, further comprising: while in vacuum control mode, adjusting vacuum supplied by the vacuum pump and controlling the flow pump to evacuate fluid from the collection chamber when a level of fluid in the collection chamber reaches a pre-selected level.

10. The method of claim 1,
    wherein monitoring the flow of irrigation fluid comprises detecting a flow rate or pressure within the irrigation line using a sensor and sending the detected flow rate or pressure to control circuitry;
    wherein monitoring the fluid level in the collection chamber comprises detecting a fluid level in the collection chamber using a fluid level sensor and sending the detected fluid level to the control circuitry;
    wherein monitoring the vacuum in the collection chamber comprises detecting a vacuum level in the collection chamber using a pressure transducer and sending the detected vacuum level to the control circuitry;
    wherein varying vacuum introduced into the chamber comprises:
       the control circuitry using the received irrigation flow rate or pressure, fluid level, and vacuum level to determine aspiration fluid flow rate; and
       the control circuitry sending a signal to the vacuum pump to increase or decrease the vacuum based on a comparison of the determined aspiration fluid flow rate and the selected flow rate.

11. A method of controlling an irrigation/aspiration system, the system having an irrigation line, an irrigation flow sensor and a vacuum pump, the vacuum pump communicating with a surgical site through a collection chamber and an aspiration line, the method comprising:
  a) connecting the irrigation line to a source of irrigation fluid;
  b) operating the vacuum pump so as to introduce a vacuum into the collection chamber so as to draw an irrigation fluid from the source of irrigation fluid through the irrigation line, the surgical site and the aspiration line and into the collection chamber;
  c) adjusting a level of fluid in the collection chamber by using a flow pump and/or the vacuum pump;
  d) monitoring a flow of the irrigation fluid in the irrigation line with the flow sensor;
  e) monitoring the fluid level in the collection chamber using a fluid level sensor;
  f) monitoring the vacuum in the collection chamber from the vacuum pump; and
  g) varying the vacuum introduced into the chamber based on the monitored irrigation fluid flow and the monitored fluid level in the collection chamber so as to maintain fluid flow into the chamber through the aspiration line at a selected flow rate;
  wherein maintaining the fluid flow at the selected flow rate is implemented for the system in a flow rate control mode and wherein the method further comprises implementing a vacuum control mode;
  wherein implementing the vacuum control mode comprises maintaining a pressure level in the aspiration line.

12. The method of claim 11, wherein implementing the vacuum control mode comprises varying the vacuum introduced into the collection chamber based on the monitored vacuum pressure and the monitored fluid level in the collection chamber so as to maintain a steady pressure level in the aspiration line.

13. The method of claim 11, wherein a flow controlled mode is maintained unless certain conditions are present in which case the vacuum controlled mode is implemented.

14. The method of claim 11, further comprising: while in vacuum control mode, adjusting vacuum supplied by the vacuum pump and controlling the flow pump to evacuate fluid from the collection chamber when a level of fluid in the collection chamber reaches a pre-selected level.

15. The method of claim 11,
  wherein monitoring the flow of irrigation fluid comprises detecting a flow rate or pressure within the irrigation line using a sensor and sending the detected flow rate or pressure to control circuitry;
  wherein monitoring the fluid level in the collection chamber comprises detecting a fluid level in the collection chamber using a fluid level sensor and sending the detected fluid level to the control circuitry;
  wherein monitoring the vacuum in the collection chamber comprises detecting a vacuum level in the collection chamber using a pressure transducer and sending the detected vacuum level to the control circuitry;
  wherein implementing the flow rate control mode to vary vacuum introduced into the chamber comprises:
    the control circuitry using the received irrigation flow rate or pressure, fluid level, and vacuum level to determine aspiration fluid flow rate; and
    the control circuitry sending a signal to the vacuum pump to increase or decrease the vacuum based on a comparison of the determined aspiration fluid flow rate and the selected flow rate;
  wherein implementing the vacuum control mode to maintain a pressure level in the aspiration line comprises:
    the control circuitry using the received vacuum level to signal a vacuum pump to adjust a vacuum supplied to the chamber; and
    based on the received fluid level, the control circuitry sending a signal to a flow pump to evacuate fluid from the chamber to maintain a steady pressure level in the aspiration line.

16. A method of controlling an irrigation/aspiration system, the system having an irrigation line, an irrigation flow sensor and a vacuum pump, the vacuum pump communicating with a surgical site through a collection chamber and an aspiration line, the method comprising:
  a) connecting the irrigation line to a source of irrigation fluid;
  b) operating the vacuum pump so as to introduce a vacuum into the collection chamber so as to draw an irrigation fluid from the source of irrigation fluid through the irrigation line, the surgical site and the aspiration line and into the collection chamber;
  c) adjusting a level of fluid in the collection chamber by using a flow pump and/or the vacuum pump;
  d) monitoring a flow of the irrigation fluid in the irrigation line with the flow sensor;
  e) monitoring the fluid level in the collection chamber using a fluid level sensor;
  f) monitoring the vacuum in the collection chamber from the vacuum pump; and
  g) varying the vacuum introduced into the chamber based on the monitored irrigation fluid flow and the monitored fluid level in the collection chamber so as to maintain fluid flow into the chamber through the aspiration line at a selected flow rate;
  wherein maintaining the fluid flow at the selected flow rate is implemented for the system in a flow rate control mode and wherein the method further comprises implementing a vacuum control mode;
  wherein a flow controlled mode is maintained unless certain conditions are present in which case the vacuum controlled mode is implemented.

17. The method of claim 16, wherein implementing the vacuum control mode comprises varying the vacuum introduced into the collection chamber based on the monitored vacuum pressure and the monitored fluid level in the collection chamber so as to maintain a steady pressure level in the aspiration line.

18. The method of claim 16, further comprising: while in vacuum control mode, adjusting vacuum supplied by the vacuum pump and controlling the flow pump to evacuate fluid from the collection chamber when a level of fluid in the collection chamber reaches a pre-selected level.

19. The method of claim 16,
  wherein monitoring the flow of irrigation fluid comprises detecting a flow rate or pressure within the irrigation line using a sensor and sending the detected flow rate or pressure to control circuitry;
  wherein monitoring the fluid level in the collection chamber comprises detecting a fluid level in the collection chamber using a fluid level sensor and sending the detected fluid level to the control circuitry;
  wherein monitoring the vacuum in the collection chamber comprises detecting a vacuum level in the collection chamber using a pressure transducer and sending the detected vacuum level to the control circuitry;
  wherein implementing the flow rate control mode to vary vacuum introduced into the chamber comprises:

the control circuitry using the received irrigation flow rate or pressure, fluid level, and vacuum level to determine aspiration fluid flow rate; and the control circuitry sending a signal to the vacuum pump to increase or decrease the vacuum based on a comparison of the determined aspiration fluid flow rate and the selected flow rate;

wherein implementing the vacuum control mode to maintain a pressure level in the aspiration line comprises:

the control circuitry using the received vacuum level to signal a vacuum pump to adjust a vacuum supplied to the chamber; and based on the received fluid level, the control circuitry sending a signal to a flow pump to evacuate fluid from the chamber to maintain a steady pressure level in the aspiration line.

* * * * *

UNITED STATES PATENT AND TRADEMARK OFFICE
CERTIFICATE OF CORRECTION

| | | |
|---|---|---|
| PATENT NO. | : 8,465,467 B2 | Page 1 of 1 |
| APPLICATION NO. | : 11/521583 | |
| DATED | : June 18, 2013 | |
| INVENTOR(S) | : Gao | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1058 days.

Signed and Sealed this
Thirtieth Day of December, 2014

Michelle K. Lee
*Deputy Director of the United States Patent and Trademark Office*